US005480969A

United States Patent [19]
Bowers et al.

[11] Patent Number: 5,480,969
[45] Date of Patent: Jan. 2, 1996

[54] ANTAGONISTS OF LHRH

[75] Inventors: Cyril Y. Bowers, New Orleans, La.; Karl A. Folkers; Anders Ljungqvist, both of Austin, Tex.; Dong-Mei Feng, Harleysville, Pa.; Anna Janceka, Austin, Tex.

[73] Assignees: The Administrators of the Tulane Educational Fund, New Orleans, La.; Board of Regents, The University of Texas System, Austin, Tex.

[21] Appl. No.: 946,056

[22] Filed: Sep. 15, 1992

[51] Int. Cl.$^6$ .............................. C07K 7/00; C07K 7/06; A61K 38/00
[52] U.S. Cl. ............................................. 530/328; 530/313
[58] Field of Search ........................ 530/328; 514/15–16

[56] References Cited

U.S. PATENT DOCUMENTS

| | | | |
|---|---|---|---|
| 2,872,484 | 2/1959 | Lecher et al. | 530/313 |
| 4,431,635 | 2/1984 | Coy et al. | 424/177 |
| 4,444,759 | 4/1984 | Rivier et al. | 424/177 |
| 4,504,414 | 3/1985 | Folkers et al. | 530/313 |
| 4,530,920 | 7/1985 | Nestor et al. | 514/15 |
| 4,647,653 | 3/1987 | Coy | 530/313 |
| 4,652,550 | 3/1987 | Rivier et al. | 514/15 |
| 4,801,577 | 1/1989 | Nestor, Jr. et al. | 514/15 |
| 4,851,385 | 7/1989 | Roeske | 514/15 |
| 4,935,491 | 6/1990 | Folkers et al. | 530/313 |
| 5,110,904 | 5/1992 | Haviv et al. | 530/313 |

FOREIGN PATENT DOCUMENTS

| | | |
|---|---|---|
| 0081877 | 6/1983 | European Pat. Off. . |
| 0097031 | 12/1983 | European Pat. Off. . |
| 0143573 | 6/1985 | European Pat. Off. . |
| 0162575 | 11/1985 | European Pat. Off. . |
| 0175506 | 3/1986 | European Pat. Off. . |
| 0197798 | 10/1986 | European Pat. Off. . |
| 0199302 | 10/1986 | European Pat. Off. . |
| 0225746 | 6/1987 | European Pat. Off. . |
| 0277829 | 8/1988 | European Pat. Off. . |
| 0328090 | 8/1989 | European Pat. Off. . |

OTHER PUBLICATIONS

Ljungqvist et al, Biochem and Biophys Res Comm, vol. 148, No. 2, 1987. pp. 849–856.
Janecka et al, Med Chem Res. 1991, 306–311.
Ljungqvist et al, vol. 46, No. 9, pp. 3297–3304 1990.
Ljungqvist et al, Design, Synthesis and Biological Evaluation of Antagonists of LHRH by Criteria of Potency, Safety and Solubility, 27 Sep. 1991 pp. 1231–1236.
Janecka, et al, *Biochem and Biophys Res. Comm* pp. 374–379, Oct. 15, 1991.
Ljungqvist et al, *PNAS*, vol. 85, pp. 8236–8240 1988.
Karten et al In Vitro Histamine Release with LHRH Analogs, Vickery & Nestor ed. MTP Press, Lancaster, UK, 1987, pp. 11–21.
Lunenfeld et al., Eds., "The Rationale and Practice of GnRH Therapy," *The Current Status of GnRH Analogues*, Parthenon Pub. Group, Park Ridge, N.J., pp. 13–17, 1991, published in USA.

Nekola et al., "Antagnoists of Luteinizing Hormone Releasing Hormone (LHRH): Potent Releasers of Histamine in Rates," *Clinical Research*, 32(5):865A, 1984, published in USA.
Hook et al., "Histamine Release by Structural Analogs of LHRH," *FASEB*, 44:1323, Abstract No. 5336, 1985, published in USA.
Miller et al., "Transdermal Iontophoresis of Gonadotropin Releasing Hormone (LHRH) and Two Analogues," *Journal of Pharmaceutical Sciences*, 79(6):490–493, 1990, published in USA.
Danforth et al., "Extended Presence of Antide (Nal-Lys GnRH Antagonist) in Circulation: Prolonged Duration of Gonadotropin Inhibition May Derive from Antide Binding to Serum Proteins," *Journal of Clinical Endocrinology and Metabolism*, 70(2):554–556, 1990, published in USA.
Horvath et al., "Synthesis and Biological Activity of LH–RH Antagonists Modified in Position 1," *Peptides*, 3:969–971, 1982, published in USA.
Folkers et al., "Advances on Chemical Structures of Effective Antagonists of the Luteinizing Hormone Releasing Hormone," *Med. Chem. Res.*, 1:235–239, 1991, published in USA.
Janecka et al., "Antagonists of the Luteinizing Hormone Releasing Hormone with Substitutions in Position 8," *Med. Chem. Res.*, 1:376–381, 1992, published in USA.
Gordon et al., "Minimal Effective Daily Dose of the GNRH Antagonist Antide Require to Achieve and Sustain Therapeutic Suppression of Estrogen Concentrations in Cynomolgue Monkeys," 73rd Annual Meeting of the American Endocrine Society, Abstract No. 1212, Jun. 19–22, 1991, published in USA.
Didolkar et al., "Effects of [derivatized]–LHRH (Nal-Lys) In Male Rats," 73rd Annual Meeting of the American Endocrine Society, Abstract No. 1704, Jun. 19–22, 1991, published in USA.
Aubert et al., "Long Lasting Inhibition of Gonadotropin Secretion by the GnRH Antagonist Antide: Evidence that Sustained GnRH Receptor Occupancy is Critical," 73rd Annual Meeting of the American Endocrine Society, Abstract No. 1688, Jun. 19–22, 1991, published in USA.
Joule et al., "Diazines: General Discussion and a Comparison with Pyridines and s–Triazine," *Heterocyclic Chemistry*, Chapter 9, pp. 123–125, Van Nostraad–Reinhold (London) 1972, published in Europe.
Roeske et al., "LHRH Antagonists with Low Histamine Releasing Activity," in *LHRH and its Analogs*, pp. 17–24, Vickery and Nestor, eds., MTP Press, Lancaster, UK (1987), published in Europe.

(List continued on next page.)

*Primary Examiner*—Jill Warden
*Assistant Examiner*—S. G. Marshall
*Attorney, Agent, or Firm*—Arnold, White & Durkee

[57] ABSTRACT

LHRH antagonists similar to antide and congeners with higher water solubility have been synthesized by substitutions in positions 1, 5 or 6 with hydrophilic residues. These peptides have antiovulatory activity with minimal histamine releasing effect.

4 Claims, No Drawings

OTHER PUBLICATIONS

Rivier et al., "LHRH Analogs as Antiovulatory Agents," in *LHRH and its Analogs*, pp. 11–22, Vickery and Nestor, eds., MTP Press, Lancaster, UK (1987), published in Europe.

Karten et al., "In Vitro Histamine Release with LHRH Analogs," *LHRH and Its Analogs; Contraceptive and Therapeutic Applications*, Part 2, eds. Vickery et al., pp. 179–190, 1987, published in England.

Humphries et al., "Inhibitory Analogues of the Luteinizing Hormone–Releasing Hormone Having D–Aromatic Residues in Positions 2 and 6 and Variation in Position 3," *Journal of Medicinal Chemistry*, 21(1):120–123, 1978, published in USA.

Janecka et al., "Design, Synthesis and Bioassays of Analogs of Argtide by Criteria of Potency and Safety," *Medicinal Chemistry Research*, 1:306–311, 1991, published in USA.

Ljungqvist et al., "Design, Synthesis and Biological Evaluation of Antagonists of LHRH by Criteria of Potency, Safety and Solubility," *Z. Naturforsch*, 46b:1231–1236, 1991, published in Europe.

Janecka et al., "Superiority of an Antagonist of the Luteinizing Hormone Releasing Hormone with Emphasis on Arginine in Position 8, Named Argtide," *Biochemical and Biophysical Research Communications*, 180(1):374–379, 1991, published in USA.

Amoss et al., "Purification, Amino Acid Composition and N–Terminus of the Hypothalamic Luteinizing Hormone Releasing Factor (LRF) of Ovine Origin," *Biochemical and Biophysical Research Communications*, 44(1):205–210, 1971, published in USA.

Bajusz et al., "New Antagonists of LHRH," *Int. J. Peptide Protein Res.*, 32:425–435, 1988, published in Europe.

Bajusz et al., "Highly Potent Antagonists of Luteinizing Hormone–Releasing Hormone Free of Edematogenic Effects," *Proc. Natl. Acad. Sci. USA*, 85:1637–1641, 1988, published in USA.

Dutta, Anand S., "Luteinizing Hormone–Releasing Hormone (LHRH) Antagonists," *Drugs of the Future*, 13(8):761–787, 1988, published in Europe.

Edelstein et al., "Single Dose Long–Term Suppression of Testosterone Secretion by a Gonadotropin–Releasing Hormone Antagonist (Antide) in Male Monkeys," *Contraception*, 42(2):209–215, 1990, published in USA.

Folkers et al., "Antagonists of the Luteinizing Hormone Releasing Hormone (LHRH) with Emphasis on the TRP$^7$ of the Salmon and Chicken II LHRH's," *Biochemical and Biophysical Research Communications*, 123(3):1221–1226, 1984, published in USA.

Folkers et al., "Increased Potency of Antagonists of the Luteinizing Hormone Releasing Hormone Which Have D–3–Pal in Position 6," *Biochemical and Biophysical Research Communications*, 137(2):709–715, 1986, published in USA.

Freidinger et al., "Bioactive Conformation of Luteinizing Hormone–Releasing Hormone: Evidence from a Conformationally Constrained Analog," *Science*, 210:656–658, 1980, published in USA.

Freidinger et al., "Protected Lactam–Bridged Dipeptides for Use as Conformational Constrainst in Peptides," *J. Org. Chem.*, 47:104–109, 1982, published in USA.

Hahn et al., "Reproductive/Endocrine and Anaphylactoid Properties of an LHRH–Antagonist, ORF 18260 [Ac–DNAL$^1$ (2), 4FDPhe$^2$, D–Trp$^3$, D–Arg$^6$]–GnRH," *Life Sciences*, 37:505–514, 1985, published in USA.

Humphries et al., "Presence of Proline in Position 3 for Potent Inhibition of the Activity of the Luteinizing Hormone Releasing Hormone and of Ovulation," *Biochemical and Biophysical Research Communications*, 72(3):939–944, 1976, published in USA.

Karten and Rivier, "Gonadotropin–Releasing Hormone Analog Design. Structure–Function Studies Toward the Development of Agonists and Antagonists: Rationale and Perspective," *Endocrine Reviews*, 7(1):44–66, 1986, published in USA.

Leal et al., "Prolonged Duration of Gonadotropin Inhibition by a Third Generation GNRH Antagonist," *Journal of Clinical Endocrinology and Metabolism*, 67(6):1325–1327, 1988, published in USA.

Leal et al., "Probing Studies on Multiple Dose Effects of Antide (NAL–LYS) GNRH Antagonist in Ovariectomized Monkeys," *Contraception*, 40(5):623–633, 1989, published in USA.

Lee et al., "Comparative Studies on the Hypotensive Effect of LHRH Antagonists in Anesthetized Rats," *Life Sciences*, 45:697–702, 1989, published in USA.

Ljungqvist and Folkers, "The Reaction of Pyridinecarboxylic Acids with Dicyclohexylcarbodiimide and p–Nitrophenol," *Acta Chemica Scandinavica*, B42:408–410, 1988, published in Europe.

Ljungqvist et al., "Design, Synthesis and Bioassays of Antagonists of LHRH Which Have High Antiovulatory Activity and Release Negligible Histamine," *Biochemical and Biophysical Research Communications*, 148(2):849–856, 1987, published in USA.

Ljungqvist et al., "Antide and Related Antagonists of Luteinizing Hormone Release with Long Action and Oral Activity," *Proc. Natl. Acad. Sci. USA*, 85:8236–8240, 1988, published in USA.

Ljungqvist et al., "Antagonists of LHRH Superior to Antide; Effective Sequence/Activity Relationships," *Tetrahedron*, 46(9):3297–3304, 1990, published in Europe.

Morgan et al., "Antagonistic Analogs of Luteinizing Hormone–Releasing Hormone Are Mast Cell Secretagogues," *Int. Archs. Allergy appl. Immun.*, 80:70–75, 1986, published in Europe.

Moroder et al., "Di–tert.–butyldicarbonat–ein vorteilhaftes Reagenz zur Einführung der tert.–Butyloxycarbonyl–Schutzgruppe," *Hoppe–Seyler's Z. Physiol. Chem.*, Bd. 357:S. 1651–1653, 1976, published in Europe.

Phillips et al., "Evaulation of the Anaphylactoid Activity of a New LHRH Antagonist," *Life Sciences*, 43:883–888, 1988, published in USA.

Rao et al., "Synthesis of 3–(3–pyridyl)– and 3–(3–benzo[b] thienyl)–D–alanine," *Int. J. Peptide Protein Res.*, 29:118–125, 1987, published in Europe.

Rivier et al., "New Effective Gonadotropin Releasing Hormone Antagonists with Minimal Potency for Histamine Release in Vitro," *J. Med. Chem.*, 29:1846–1851, 1986, published is USA.

Schally et al., "Gonadotropin–Releasing Hormone: One Polypeptide Regulates Secretion of Luteinizing and Follicle–Stimulating Hormones," *Science*, 173:1036–1038, 1971, published in USA.

Schmidt et al., "[Ac–D–NAL(2)$^1$, 4FD–Phe$^2$, D–Trp$^3$, D–Arg–$^6$]–LHRH, A Potent Antagonist of LHRH, Produces Transient Edema and Behavioral Changes in Rats," *Contraception*, 29(3):283–289, 1984, published in USA.

Sundaram et al., "Antagonists of Luteinizing Hormone

Releasing Hormone Bind to Rat Mast Cells and Induce Histamine Release," *Agents and Actions*, 25(3/4):307–313, 1988, published in Europe.

Tjoeng et al., "Vier Synthesewege zu (2–Pyrimidinylamino)–n–alkansäuren," *Chem. Ber.*, 108:862–874, 1975, published in Europe.

Benoiton, Leo, "Amino Acids and Peptides," *Canadian Journal of Chemsitry*, 42:2043–2047, 1964, published in Canada.

Prasad et al., "Structure–Activity Relationships in Luteinizing Hormone–Releasing Hormone," *Journal of Medicinal Chemistry*, 19(4):492–495, 1976, published in USA.

Fife and Przystas, "Divalent Metal Ion Catalysis in the Hydrolysis of Esters of Picolinic Acid. Metal Ion Promoted Hydroxide Ion and Water Catalyzed Reactions," *J. Am. Chem. Soc.*, 107:1041–1047, 1985, published in USA.

Bernardi et al., "An Experimental Approach to Long–Lasting Hypotensive Eledoisin–Like Peptides," *J. Pharm. Pharmac.*, 19:95–101, 1967, published in Europe.

Petermann and Fauchère, "Synthesis of β–Pyrazinyl–L–Alanine (Paa)$^1$) and of Peptide Derivatives," *Helvetica Chimica Acta*, 66(5):1513–1518, published in Europe 1983.

Folkers et al., "Activities of Antagonists of the Luteinizing Hormone Releasing Hormone with Emphasis on Positions 1, 5 and 6 and on Positions 1, 2 and 3," *Z. Naturforsch, B: Chem. Sci.*, 42(1):101–106, 1987, published in Europe.

Hocart et al., "Effect of Reductive Alkylation of Lysine in Positions 6 and/or 8 on the Histamine–Releasing Activity of Luteinizing Hormone–Releasing Hormone Antagonists," *J. Med. Chem.*, 30(10):1910–1914, 1987, published in USA.

Hocart et al., "Effect of Reductive Alkylation of D–Lysine in Position 6 on the Histamine–Releasing Activity of Luteinizing Hormone–Releasing Hormone Antagonists," *J. Med. Chem.*, 30:739–743, 1987, published in USA.

Roeske and Chaturvedi, "Substituion of Arg$^5$ for Tyr$^5$ in GNRH Antagonists," *Peptides: Structure and Function*, Proceedings of the 9th American Pep. Sym., C. M. Deber, V. J. Hruby, K. D. Kopple (Editors), Pierce Chem. Co., Rockford, Ill., pp. 561–564, Feb. 13, 1986, published in USA.

Leal et al., "Persistent Suppression of Gonadotropin Secretion by a Single Dose of 3rd Generation GnRH Antagonists in Primates," Abstract No. 883, name, date and place of publication unknown.

Channabasavaiah and Stewart, "New Analogs of Luliberin Which Inhibit Ovulation in the Rat," *Biochemical and Biophysical Research Communication*, 86(4):1266–1273, 1979, published in USA.

Channabasavaiah et al., "New Potent Agonist and Antagonist Analogs of Luteinizing Hormone Releasing Hormone," pp. 803–806, name and place of publication unknown 1979.

Nikolics and Spona, "In Vitro LH Release and cAMP Accumulation Induced by Synthetic GnRH Derivatives," *Peptides*, 5:1001–1006, 1984, published in USA.

Rivier et al., "GnRH Antagonists: N–Alkylation of Primary Amino Functions Generate New Potent Analogs," *Coll. Soc. Fr. Etudes Fertil.*, 26:25–31, 1988, published in Europe.

ANTAGONISTS OF LHRH

This invention was made with government support under contract no. NO1-HD-1-3101 awarded by the National Institutes of Health. The government has certain rights in the invention.

BACKGROUND OF THE INVENTION

Many potent antagonists of LHRH (the luteinizing hormone releasing hormone, pGlu,His,Trp,Ser,Tyr,Gly,Leu, Arg,Pro,Gly-NH$_2$) have structural features which cause release of histamine from mast cells [Karten et al., 1986]. These features include a group of hydrophobic amino acids at the N-terminal and strongly basic residues in positions 6 and 8, notably D-Arg$^6$, Arg$^8$. A prime example of this class of antagonists is [N-Ac-D-2-Nal$^1$,D-4F-Phe$^2$D-Trp$^3$,D-Arg$^6$]-LHRH [Schmidt et al.]. Some antagonists bind to rat peritoneal mast cells and membrane preparations and that the binding was related to the release of histamine [Sundaram et al.].

| Abbreviations for the unnatural amino acids mentioned herein |
|---|
| Abu = 2-aminobutyric acid |
| (AcDSer)Lys = N$^\epsilon$-(N-acetyl-D-seryl)lysine |
| (DSer)Lys = N$^\epsilon$-(D-seryl)lysine |
| 2-Nal = 3-(2-naphthyl)alanine |
| 3-Pal = 3-(3-pyridyl)alanine |
| 3-Qal = 3-(3-quinolyl)alanine |
| AOPP = 2-(3 1-amino-2'-oxo-1'-pyrrolidino)-4-methylpentanoic acid |
| Aze = azetidine-2-carboxylic acid |
| Cit = citrulline |
| Cl$_2$Phe = 3-(3,4-dichlorophenyl)alanine |
| cPzACAla = cis-3-(4-pyrazinylcarbonylaminocyclohexyl)alanine |
| ILys = N$^\epsilon$-isopropyllysine |
| NicLys = N$^\epsilon$-nicotinoyllysine |
| p-FPhe = 3-(4-fluorophenyl)alanine |
| pClPhe = 3-(4-chlorophenyl)alanine |
| PicLys = N$^\epsilon$-picolinoyllysine |
| Ptf = 3-(4-trifluoromethylphenyl)alanine |
| PzAla = 3-pyrazinylalanine |
| PzAPhe = 3-(4-pyrazinylcarbonylaminophenyl)alanine |
| PzcLys = N$^\epsilon$-pyrazinylcarbonyllysine |
| PzLys = N$^\epsilon$-pyrazinylcarbonyllysine |

The present inventors have recently developed Antide (analog 1, Table III) which lacked strongly basic residues and which showed high potency and negligible histamine release [Ljungqvist et al, 1987]. Further evaluation of the anaphylactoid activity of Antide showed that Antide "represents a new generation of LHRH antagonists with an improved safety margin" [Phillips et al.].

Prolonged duration of inhibition of gonadotropin secretion in overectomized monkeys using single [Leal et al.1988] or multiple [Leal et al, 1989] doses of Antide has also been established.

The same group observed a long-term suppression of testosterone secretion in male monkeys after a single dose of Antide [Edelstein et al.].

The mechanism(s) for this long-term action of Antide seems to include binding to serum proteins for a peripheral depot effect, and structural stability to enzymic cleavage. Binding to proteins was shown by studies using a radioreceptor assay [Danforth et al.].

If a depot effect, regardless of mechanism, is at least partially responsible for the long duration of action of Antide, the relatively poor water solubility at physiological pH may actually be an advantage. There are, however, reports that low water solubility has caused problems [Lee et al., Miller et al.].

It was thus considered of importance to modify Antide and some potent analogs [Ljungqvist et al., 1987; Ljungqvist et al., 1988] in order to increase their water solubility and to study how this would effect the biological activities of the resulting analogs.

Lunenfield et al. summarized four different rationales for potential therapy of clinical modalities. They are: (1) to suppress steroid-dependent mechanisms of malignancies and endometriosis; (2) to inhibit precocious puberty, etc.; (3) to control gonadotropin secretion in ovulation, etc.; (4) to exploit other effects depending upon future proof of applicability. The existing wide-scale clinical use of LHRH agonists is a background for potential uses of antagonists, but the lower activities of antagonists, by one-thousandth that of agonists means that per unit dose the potency of the presently known antagonists need to be increased up to ten-fold for promising clinical use.

In the early years, antagonists such as [D-Phe$^2$, Pro$^3$, DTrp$^6$] LHRH (Humphries et al., 1976) showed AOA$_{100}$ at 750 μg/rat. Introduction of basic D-amino acids in position 6 resulted in a significant increase of antiovulatory activity. Antagonists like [N-Ac-D-2-Nal$^1$; D-pClPhe$^2$, D-Trp$^3$, D-Arg$^6$, D-Ala$^{10}$] LHRH by Horvath et al and [N-Ac-D-2-Nal$^1$, D-pClPhe$^2$, D-3-Pal$^3$, D-Arg$^6$, Trp$^7$, D-Ala$^{10}$] LHRH by Folkers et al. (1984) were examples of antagonists with AOA (antiovulatory activity) of 100% at ca. 0.5 μg/rat.

However, the most potent D-Arg$^6$-containing antagonists produced edema in the face and extremities [Schmidt et al.; Morgan et al.] and a dose-related wheal response [Hahn et al.]. These undesired effects apparently caused by release of histamine from mast cells [Hook et al.] have been ascribed to the presence of strongly basic residues in position 6 and 8, e.g., D-Arg$^6$, Arg$^8$, and a cluster of hydrophobic amino acids at the N-terminal [Nikola et al., Roeske et al.].

With new emphasis on decreasing the histamine releasing activity, structural modification of antagonists was focused primarily on reducing basicity in positions 6 and 8. This goal was achieved by different approaches. Folkers et al. 1986, introduced D-3-Pal$^6$ instead of D-Arg$^6$ and obtained the relatively potent antagonist [N-Ac-D-2-Nal$^1$, D-pClPhe$^2$, D-3-Pal$^3$, Arg$^5$, D-3-Pal$^6$, D-Ala$^{10}$] LHRH, but the histamine release was undesirable. Suppression of histamine release occurred by introduction of D-ureidoalkyl amino acids such as D-citrulline or D-homocitrulline at position 6 by Bajusz et al., but the most active antagonist of their series [N-Ac-D-2-Nal$^1$, DpClPhe$^2$, D-Trp$^3$, D-Cit$^6$, D-Ala$^{10}$] LHRH, caused 100% AOA in doses as high as 3 μg/rat.

Combining aspects of safety and AOA was achieved by Ljungqvist et al., 1987, with a new class of antagonists which featured acylated Lys residues in positions 5 and 6 in combination with alkylated Lys in position 8. The prominent example of this class of antagonists is Antide, [N-Ac-D-2-Nal$^1$, D-pClPhe$^2$, D-3-Pal$^3$, NicLys$^5$, D-NicLys$^6$, Ilys$^8$, D-Ala$^{10}$] LHRH which completely inhibited ovulation at 1 μg/rat and had an ED$_{50}$ for histamine release 300 μg/ml. Antagonists with AOA superior to Antide with acylated aminocyclohexylalanines and acylated lysines in position 5 and 6 were next reported; Ljungqvist et al., 1990.

The synthesis and bioassays of some new analogs with improved water solubility and biological effectiveness are described herein.

Antagonists of the hypothalamic luteinizing hormone releasing hormone (LHRH), decapeptide, pClu,His,Trp,Ser, Tyr,Gly,Leu,Arg,Pro,GlyNH$_2$, have been proposed for use in the control of fertility and in the treatment of hormone dependent tumors. A few thousand analogs of LHRH have been reported since its structure was elucidated in 1971

[Amoss et al., Schally et al.]. The first thirteen years witnessed the development of the Nal-Arg generation of antagonists [Karten et al., 1986], but they were also potent, in vitro, to release histamine [Schmidt et al.]. With that knowledge, emphasis was then placed on reducing the histamine releasing potency while maintaining or preferably increasing gonadotropin suppressive potency.

SUMMARY OF THE INVENTION

LHRH antagonists similar to antide and congeners with higher water solubility have been synthesized by substitutions in positions 1, 5 or 6 with hydrophilic residues. In position I, D-3-Qal has been incorporated in four peptides and D-3-Pal in one peptide. In positions 5 and 6, D and L-3-Pal, PzAla and (DSer)Lys have been tried. In one peptide, D-(AcDSer)Lys was substituted in position 6. Most of the new analogs had lower AOA (antiovulatory activity) than the parent compounds but three potent analogs were identified. The first one:

[N-Ac-D-3-Qal$^1$,D-pClPhe$^2$,D-3-Pal$^3$,cPzACAla$^5$,D-PicLys$^6$,ILys$^8$, D-Ala$^{10}$] -LHRH, had 55% AOA at 0.25 µg and 100% at 0.5 µg. Its ED$_{50}$ for in vitro histamine release was 171±17 µg/ml which is an increase from 49±4.8 µg/ml for the parent compound with N-Ac-D-2-Nal[1]. The second analog:

[N-Ac-D-Nal$^1$,D-pClPhe$^2$,D-3-Pal$^3$,PicLys$^5$,D-(DSer)Lys$^6$, ILys$^8$,D-Ala$^{10}$]-LHRH, had 69% AOA at 0.25 µg and 95% at 0.5 µg. This analog released somewhat more histamine than the parent analog featuring D-PicLys$^6$, the ED$_{50}$ being 18 µg/ml compared to 93±11 for the parent analog. The third analog is:

[N-Ac-D-2-Nal$^1$,D-pClPhe$^2$,D-3-Pal$^3$,c-PzACAla$^5$,D-PzAla$^6$,ILys$^8$,DAla$^{10}$]-LHRH.

The AOA for this analog was 63% at 0.25 µg and the ED$_{50}$ for histamine release 88±6.4 µg/ml. In the research for more potent antagonists of the luteinizing hormone releasing hormone (LHRH), new peptides with emphasis on arginine in position 8 were designed, synthesized and tested for anti-ovulatory activity (AOA). Very potent analogs were achieved. N-Ac-D-3-Qal, D-pClPhe, D-3-Pal, Ser, c-PzACAla, D-PicLys, Leu, Arg, Pro, D-AlaNH$_2$ showed 63% AOA at 0.125 µg and 89% at 0.25 µg, and an ED$_{50}$ of 30.8±0.59 and presently may be the most promising antagonist reported. It is named Argtide. N-Ac-D-3-Qal, D-pClPhe, D-3-Pal, Ser, c-PzACAla, D-PicLys, Val, Arg, Pro, D-AlaNH$_2$ showed 18% AOA at 0.125 µg. Arg$^8$ in antagonists may be significant for receptor binding.

Thirteen analogs of the LHRH antagonist, named Argtide, N-Ac-D-3-Qal, D-pClPhe, D-3-Pal, Ser, c-PzACAla, D-PicLys, Leu, Arg, Pro, D-AlaNH$_2$ with single changes in its sequence have been synthesized toward an increase in potency and/or decreases in histamine release. One of the most potent of the new analogs is [D-Ptf$^2$]-Argtide which showed 20% anti-ovulatory activity (AOA) at 0.125 µg and 100% at 0.25 µg, and which is superior to Antide. One of the most safe analog in terms of histamine release was [Cit$^5$]-Argtide which showed an ED$_{50}$ 94 µg/ml. D-3-Qal was frequently superior to D-2-Nal in position 1.

DESCRIPTION OF THE PREFERRED EMBODIMENTS

EXAMPLE 1

DESIGN, SYNTHESIS AND BIOLOGICAL EVALUATION OF ANTAGONISTS OF LHRH BY CRITERIA OF POTENCY, SAFETY AND SOLUBILITY

Experimental
Materials

BOC-Ser(OBzl), BOC-Pro, BOC-Leu and BOC-D-Ala were obtained from Peninsula Laboratories, Belmont, Calif. Abu was obtained from Sigma Chemical Company, St. Louis, Mo. and it was converted to the BOC-derivative using standard procedures [Moroder et al.].

BOC-D-2-Nal, BOC-D-pClPhe, BOC-D- and L-3-Pal, BOC-ILys(Z) dicyclohexylamine salt, BOC-D- and L-NicLys and BOC-D-3-Qal were all provided by Dr. Narasimha Rao of the Southwest Foundation for Biomedical Research, San Antonio, Tex. BOC-D- and L-PzAla were synthesized by literature methods [Peterman et al.].

BOC-AOPP was kindly provided by Dr. R. M. Freidinger, Merck, Sharp & Dohme, West Point, Pa. [Freidinger et al., 1980 and 1982]. α-BOC-cis-D- and L-4-amino-cyclohexylalanine were provided by Dr. Narasimha Rao, and were converted to the corresponding BOC-cis-D- and L-PzACAla derivatives by acylation with the p-nitrophenylester [Folkers et al, 1990] of pyrazinecarboxylic acid from the Aldrich Chemical Company, Milwaukee, Wis., in DMF.

BOC-D- and L-PicLys were similarly prepared from α-BOC-D- and L-Lys and picolinic acid p nitrophenylester [Ljungqvist et al., 1988a] in DMF. α-BOC-D- and L-(DSer)Lys, protected at the D-Set moiety by the Z group at the amino group and by the benzyl group at the hydroxyl function, were synthesized by acylation of BOC-D- and L-Lys in DMF by Z-D-Ser(OBzl)-ONp in the presence of 1-hydroxybenzotriazole. The BOC-D-(AcDSer)Lys, protected as the benzyl derivative at the D-Ser hydroxy, was similarly prepared by the reaction between Ac-D-Ser(OBzl)ONp and BOC-D-Lys.

All synthesized amino acids and intermediates were characterized by NMR and were homogenous on TLC.

The benzhydrylamine hydrochloride resin was purchased from Beckman Bioproducts, Palo Alto, Calif. The dicyclohexylcarbodiimide was from Ald-rich and was distilled in vacuo before use. The dichloromethane was distilled from sodium carbonate. All other solvents and reagents were reagent grade.

Synthesis

The peptides were synthesized by the solid-phase method using a Beckman automated 990 peptide synthesizer. The protocol details used were essentially as described [Folkers et al., 1984]. The peptide was cleaved from the resin with concomitant removal of all protecting groups by treatment with doubly distilled HF at 0° C. for 1 h in the presence of about 10% anisole in p-cresol. The HF was then evaporated, in vacuo, first by a water aspirator and then by pump vacuum overnight. The residue was then extracted 2–3 times with ether in order to remove non-peptidic material. The crude peptide was subsequently extracted with aqueous acetic acid and the extract was lyophilized.

Purification and Characterization

Purification was achieved by chromatography on $SiO_2$ (EM, 230–400 mesh) with the solvent system n-butanol:acetic acid:water 4:1:2 or 4:1:5 (upper phase) followed by gel filtration on Sephadex G 25 with 6% aqueous acetic acid as the eluant. An alternative purification method was gel filtration as above followed by chromatography on Sephadex LH 20 with the solvent system water:butanol:acetic acid:methanol 90:10:10:8.

The purity was checked by TLC, amino acid analysis and HPLC.

Amino acid analyses were carried out on a Beckman 118 CL amino acid analyzer after hydrolysis in constant boiling HCl for 24 h using standard procedures [Folkers et al., 1984]. The unnatural amino acids were qualitatively determined with the exception of 3-Pal which was quantified. The data are in Table II.

TABLE II

Amino acid analyses.

| # | Ser | Pro | Ala | Leu | Lys | 3-Pal | ILys | 2-Nal | pClPhe | Others |
|---|---|---|---|---|---|---|---|---|---|---|
| 2. | 0.90 | 0.98 | 1.03 | 1.00 | 1.88 | 0.90 | + | | + | 3-Qal+ |
| 3. | 1.00 | 0.94 | 1.04 | 1.00 | 1.05 | 0.96 | + | + | + | PzAla+ |
| 4. | 2.05 | 1.10 | 1.05 | 0.99 | 1.90 | 0.90 | + | + | + | |
| 6. | 1.94 | 1.00 | 0.90 | 1.00 | 1.98 | 1.00 | + | + | + | |
| 7. | 1.92 | 1.00 | 1.06 | 0.98 | 2.01 | 1.02 | + | + | + | |
| 8. | 1.96 | 0.96 | 1.02 | 1.01 | 2.03 | 1.00 | + | + | + | |
| 9. | 1.04 | 0.91 | 1.07 | 1.01 | 0.92 | 0.99 | + | + | + | PzAla+ |
| 11. | 0.91 | 0.96 | 1.11 | 0.97 | 1.00 | 1.03 | + | | + | ACAla*+3-Qal+ |
| 12. | 0.97 | 0.87 | 1.16 | 1.04 | 0.96 | 1.99 | + | | + | ACAla+ |
| 13. | 1.00 | 0.94 | 1.04 | 1.00 | | 1.00 | + | + | + | PzAla+ACAla+ |
| 14. | 0.91 | 0.92 | 0.94 | 0.97 | | 2.01 | + | + | + | ACAla+ |
| 15. | 1.93 | 1.09 | 1.07 | 1.00 | 1.01 | 0.90 | + | + | + | ACAla+ |
| 16. | 0.81 | 1.11 | 1.13 | 1.01 | | 1.92 | + | + | + | ACAla+ |
| 18. | 0.98 | 0.98 | 1.00 | 1.02 | | 1.01 | + | + | + | ACAla+PzAla+ |
| 20. | 0.92 | 0.96 | 1.10 | | 1.94 | 1.06 | + | | + | 3-Qal+Abu+ |
| 21. | 0.89 | 0.97 | 1.12 | | 1.00 | 1.02 | + | + | + | AOPP**+ |
| 22. | 0.94 | 1.01 | 1.05 | | 0.95 | 1.02 | + | | + | AOPP+,3-Qal+ |

5*ACAla = 4-aminocyclohexylalanine; **AOPP is hydrolyzed to yield two peaks, one of which may be lactam acid with a free amino group and other may be the acid with the lactam ring hydrolyzed.

The peptides gave single spots on TLC (EM, 0.25 mm $SiO_2$) in four different solvent systems (Table I).

TABLE I

TLC data.

| # | Rf1 | Rf2 | Rf3 | Rf4 | Rf5 |
|---|---|---|---|---|---|
| 2. | 0.68 | 0.32 | 0.48 | 0.54 | |
| 3. | 0.70 | 0.35 | | 0.74 | 0.84 |
| 4. | 0.55 | 0.38 | | 0.43 | 0.73 |
| 6. | 0.62 | 0.38 | | 0.47 | 0.77 |
| 7. | 0.58 | 0.33 | | 0.45 | 0.75 |
| 8. | 0.62 | 0.35 | | 0.53 | 0.80 |
| 9. | 0.69 | 0.34 | | 0.78 | 0.85 |
| 11. | 0.74 | 0.35 | 0.48 | 0.62 | |
| 12. | 0.70 | 0.37 | 0.39 | 0.53 | |
| 13. | 0.68 | 0.32 | | 0.76 | 0.84 |
| 14. | 0.67 | 0.31 | | 0.76 | 0.83 |
| 15. | 0.61 | 0.39 | | 0.42 | 0.75 |
| 17. | 0.68 | 0.35 | | 0.71 | 0.78 |
| 18. | 0.69 | 0.38 | | 0.73 | 0.68 |
| 20. | 0.64 | 0.33 | | 0.50 | 0.81 |
| 21. | 0.71 | 0.41 | | 0.55 | 0.82 |
| 22. | 0.66 | 0.37 | | 0.53 | 0.81 |

Solvent systems:
1. n-BuOH:py:HOAc:$H_2O$ = 4:1:1:2;
2. n-BuOH:HOAc:$H_2O$ = 4:1:2;
3. n-BuOH:py:HOAc:$H_2O$ = 40:1:10:20;
4. n-BuOH:py:HOAc:$H_2O$ = 30:10:3:12;
5. EtOAc:py:HOAc:$H_2O$ = 5:5:1:3.

The purity was further checked by HPLC using a Waters instrument with a 660 solvent programmer and a Vydac $C_{18}$ column. The flow rate was 1.5 ml/min and the absorbance was recorded at 210 nm. Different gradients of increasing concentration of acetonitrile in 0.01M $KH_2PO_4$, adjusted to pH 3 with $H_3PO_4$, were employed. All peptides were estimated to be 97–99% pure in this system (data not shown).

Biological assays

AOA in rats was determined as reported [Humphries et al.]. The wheal area/10 µg of analog was calculated as described [Ljungqvist et al. 1987]. The histamine release was assayed in rat mast cells as reported [Hook et al., Karten et al. 1987]. The $ED_{50}$ value reported is the concentration in µg/ml that releases 50% of total releasable histamine. The biological data are in Table III.

TABLE III

Biological data for LHRH antagonists of the general sequence:
N—Ac—Xaa$^1$, DpClPhe$^2$, D-3-Pal$^3$, Ser$^4$, Yaa$^5$Zaa$^6$, Waa$^7$, ILys$^8$, Pro$^9$, D—Ala$^{10}$—NH$_2$

| # | Xaa | Yaa | Zaa | Waa | AOA %/µg 0.125 | AOA %/µg 0.25 | ED$_{50}$ for hist. release 0.5 µg/ml | Wheal area mm$^2$/10 µg |
|---|-----|-----|-----|-----|-----|-----|-----|-----|
| 1.$^{a*}$ | D-2-Nal | NicLys | D-NicLys | Leu | — | 0 | 36 >300 | 132.7 ± 0 |
| 2. | D-3-Qal | NicLys | D-NicLys | Leu | — | — | 0 | 88.8 ± 4.0 |
| 3. | D-2-Nal | NicLys | D-PzAla | Leu | — | 0 | 88 | 83.0 ± 7.5 |
| 4. | D-2-Nal | NicLys | D-(DSer)Lys | Leu | — | 0 | 30 26 ± 3.4 | 81.2 ± 2.7 |
| 5. | D-2-Nal | PicLys | D-PicLys | Leu | — | 40 | 100 93 ± 11 | 123.0 ± 0 |
| 6. | D-2-Nal | (DSer)Lys | D-PicLys | Leu | — | — | 13 22 ± 4.7 | 106.9 ± 3.1 |
| 7. | D-2-Nal | PicLys | D-(DSer)Lys | Leu | 20 | 69 | 95 18 | 103.9 ± 5.2 |
| 8. | D-2-Nal | PicLys | D-(AcDSer)Lys | Leu | — | 0 | — 53 ± 11 | 97.2 ± 2.2 |
| 9. | D-2-Nal | PicLys | D-PzAla | Leu | — | 9 | — | 115.4 ± 2.4 |
| 10.$^b$ | D-2-Nal | c-PzACAla | D-PicLys | Leu | — | 67 | 90 49 ± 4.8 | 99.5 ± 4.5 |
| 11. | D-3-Qal | c-PzACAla | D-PicLys | Leu | 17 | 55 | 100 171 ± 17 | 82.9 ± 7.0 |
| 12. | D-3-Pal | c-PzACAla | D-PicLys | Leu | — | 20 | — | 118 |
| 13. | D-2-Nal | c-PzACAla | D-PzAla | Leu | — | 63 | — 88 ± 6.4 | 120.6 ± 7.3 |
| 14. | D-2-Nal | c-PzACAla | D-3-Pal | Leu | — | 44 | — 68 ± 1.8 | 113.1 ± 3.9 |
| 15. | D-2-Nal | c-PzACAla | D-(DSer)Lys | Leu | — | 11 | — | 117.8 ± 2.8 |
| 16.$^b$ | D-2-Nal | PicLys | c-D-PzACAla | Leu | 29 | 73 | 100 28 ± 7.5 | 122.8 ± 5.7 |
| 17. | D-2-Nal | 3-Pal | c-D-PzACAla | Leu | — | 33 | — 16 ± 2.0 | 101.7 ± 4.3 |
| 18. | D-2-Nal | PzAla | c-D-PzACAla | Leu | — | 44 | 28 ± 4.7 | 101.6 ± 2.2 |
| 19.$^b$ | D-2-Nal | PicLys | D-PicLys | Abu | — | 36 | 100 273 ± 27 | 92.0 ± 5.4 |
| 20. | D-3-Qal | PicLys | D-PicLys | Abu | — | 0 | — | 103.9 ± 3.7 |
| 21. | D-2-Nal | PicLys | AOPP | — | — | 44 | 71 | 99.5 ± 4.5 |
| 22. | D-3-Qal | PicLys | AOPP | — | — | 0 | — | 89.5 ± 5.5 |

$^a$From Ljungqvist, er al. 1987;
$^b$from Ljungqvist et al. 1986;
*Antide.

Single-residue changes were made in analogs with good potency. Positions 1, 5 and 6 were chosen for these changes. Position 1 is D-2-Nal in five analogs selected for this study. D-2-Nal has been a dominant substituent in position 1 for some time [Dutta], and its very lipophilic character made it a suitable candidate for substitution. D-3-Qal which is isosteric with D-2-Nal but much more hydrophilic was chosen as a replacement. In one peptide, D-3-Pal was placed in position 1.

In Antide and its congeners, positions 5 and 6 are occupied by a new class of amino acids, acylated lysines and amino-cyclohexylalanines. Since in earlier analogs, these positions were often occupied by basic, hydrophilic residues [Dutta], the relatively poor water solubility of Antide and its analogs may be, at least partly, attributed to these residues.

In positions 5 and 6, the more hydrophilic amino acids, D- and L-3-Pal, PzAla, (DSer)Lys and D-(AcDSer)Lys were used.

Substitutions in position 1

D-2-Nal has been replaced by D-3-Qal in four peptides. In Antide (analog 1) the AOA decreased from 36 to 0% at 0.5 µg (analog 2). The wheal area decreased considerably from 132.7 to 8.8 mm[Schmidt et al.].

When D-3-Qal was incorporated into analog 10 [Ljungqvist et al., 1988] the AOA potency remained high, 55% at 0.25 µg and 17% at 0.125 µg. Even more interesting, however, may be the observation that the ED$_{50}$ for histamine release increased from 49 to 171 µg/ml and the wheal area is small, only 82.9 mm. These data support the concept that a very lipophilic N-terminal promotes histamine release. Analog 11 may have a high margin of safety.

Analog 19 with Abu in position 7 [Ljungqvist et al., 1988] and analog with AOPP [Freedinger et al., 1980, 1982] in positions 6–7 have also been substituted with D-3-Qal in position 1. The resulting analogs 20 and 22 were both inactive at 0.25 µg as compared to AOA values of 36 and 44% for the parent compounds.

In summary, four peptides have been substituted with D-3-Qal in position 1. One retained its potency, and the other three showed no activity at the level tested. The analog that retained its potency had the largest lipophilicity of the group, featuring c-PzACAla$^5$,D-PicLys$^6$,Leu$^7$. Antide has NicLys$^5$, D-NicLys$^6$,Leu$^7$. Analog 19 has PicLys$^5$,AOPP$^{6,7}$ which lacks the long acylated side chain normally present in position 6. These three latter peptides lost their AOA upon replacement of D-2-Nal by D-3-Qal. Consequently, it seems that in order for the hydrophilic quinolylalanine to be effective, its hydrophilicity should be balanced by increased lipophilicity elsewhere in the molecule.

Analog 12 has the considerably smaller D-3-Pal instead of D-2-Nal in position 1. The AOA decreased to 20% at 0.25 µg, but taking into account the structural difference between D-2-Nal and D-3-Pal, the value of 20% is noteworthy.

Substitutions in position 5

Analog 6 has PicLys$^5$ in the parent analog (5)[Ljungqvist et al., 1987] replaced by (DSer)Lys. This change caused a large decrease in potency, and the AOA was 13 and 0% at 0.5 and 0.25 µg, respectively, as compared to 100 and 40% for analog 5. The ED$_{50}$ for histamine release was decreased fourfold, from 93 to 22 µg/ml. This result is not surprising since (DSer)Lys contains a basic amino group and PicLys does not.

The very potent analog 16 [Ljungqvist et al., 1988], with the c-D-PzACAla moiety in position 6 has been modified in position 5 with 3-Pal and PzAla (analogs 17 and 19). Both substitutions reduced the potency to about one-half or from 73% to 33 and 44%, respectively, at 0.25 µg. The analogs did, however, retain considerable activity. The $ED_{50}$ value was reduced from 28 to 16 for the 3-Pal$^5$ analog, but the corresponding value for the analog with the much less basic [Joule et al.] PzAla remained unchanged.

Substitutions in position 6

D-PzAla has been incorporated in position 6 in Antide (analog 1), analog 5 and analog 10. In the case of Antide, a considerable increase in potency was noted at 0.5 µg, 88 vs. 36% (analog 3). At 0.25 µg, like Antide, analog 3 was however inactive. Its wheal area was notably small, 83 mm$^2$.

In analog 5, the same substitution caused a substantial decrease in potency, 9 vs. 40% at 0.25 µg (analog 9), but analog 13 was equipotent with its parent compound 10, 64 vs. 67% at the same dose level. It is evident that the same amino acid residue can cause widely different effects on AOA depending on the sequence in which it is introduced.

Of importance is the lowering of histamine release by D-PzAla$^6$ introduction into analog 13; the $ED_{50}$ increased from 49 to 88 µg/ml.

In analog 14, D-3-Pal$^6$ replaced D-PicLys$^6$ in the sequence of analog 10. This change lowered AOA moderately, from 67 to 44% at 0.25 µg, but the $ED_{50}$ for histamine release increased from 49 to 68 µg/ml. D-PzAla may be slightly better then D-3-Pal in position 6.

D-(DSer)Lys has been incorporated in position 6 of the three peptides 1, 5 and 10. Analog 4, based on Antide, was equipotent, 30% AOA at 0.5 µg. The histamine release increased by a factor 10; the $ED_{50}$ being 26 µg/ml compared with 300 µg/ml for Antide. Compound 7, based on analog 5, showed increased potency, 69 vs. 40% at 0.25 µg. It had 20% AOA at 0.125 µg. The $ED_{50}$ value was about 18, that is it released more histamine than be parent compound, analog 5 with D-PicLys$^6$. Analog 7 with D-(DSer)Lys$^6$ had high potency. As a comparison, analog 16, featuring the usually very effective c-PzACAla$^5$ had only 11% AOA at 0.25 µg. It seems that the (DSer)Lys moiety is effective only if very specific structural features are present in the rest of the chain [25]. The high potency of analog 7 is also remarkable in comparison with analog 6 which has (DSer)Lys in position 5 and was inactive at 0.25 µg. The latter analog was designed toward reducing histamine release by moving the basic residue from position 6 to position 5 according to Rivier et al.. The $ED_{50}$ value for analog 6 was, however, 22 compared to 18 for analog 7, that is they are very similar.

Analog 8 has D-(AcDSer)Lys in position 6. This peptide was designed in order to learn if histamine release would be affected upon acetylation of the serine amino group. This was the case. The $ED_{50}$ for 8 was 53, an increase from the value of 18 for analog 7. The wheal areas are also very similar, 97.2 vs. 103.9 mm$^2$. Analog 8 was inactive at 0.25 µg which indicates that the basicity may be necessary in this residue for good AOA potency.

EXAMPLE 2

SUPERIORITY OF AN ANTAGONIST OF THE LUTEINIZING HORMONE RELEASING HORMONE WITH EMPHASIS ON ARGININE IN POSITION 8, NAMED ARGTIDE

Described herein are the design, synthesis and bioassay data on new antagonists of LHRH, toward the goal of a ten-fold increase in potency. Since there are no established guidelines for design for a high probability of increased potency, many alternatives of design are required in the hope that greatly increased potency will be unpredictably achieved. Two of 13 antagonists have activities at dosages of 0.125 µg. One of these antagonists may be comparable to the most potent antagonists reported in the literature to date. This antagonist, named Argtide, is [N-Ac-D-2-Nal$^1$, D-pClPhe$^2$, D-3-Pal$^3$, c-PzACAla$^5$, D-PicLys$^6$, D-Ala$^{10}$] LHRH and it showed 63% AOA at 0.125 µg and 89% AOA at 0.25 µg.

Materials:

The natural amino acids were obtained from Peninsula Laboratories, San Carlos, Calif. BOC-Abu was purchased from Sigma Chemical Co., St. Louis, Mo. BOC-D-2-Nal, BOC-D-3-Qal, BOC-D-pClPhe, BOC-D- and L-3-Pal were provided by Dr. Narashima Rao of the Southwest Foundation for Biomedical Research, San Antoni, Tex. α-BOC-cis-L-aminocyclohexylalanine, from Dr. Narashima Rao, was converted to the corresponding BOC-cis-L-PzACAla derivative by Acylation with the p-nitrophenylester (16) of pyrazinecarboxylic acid from the Aldrich Chemical Co., Milwaukee, Wis., in DMF. BOC-D- and L-PicLys and BOC-PzcLys were similarly prepared from BOC-D- and L-Lys and picolinic acid (17) or, pyrazine carboxylic acid p-nitrophenylester in DMF. The benzhydrylamine hydrochloride resin was purchased from Advanced Chem. Tech., Louisville, Ky. The dicyclohexylcarbodiimide was distilled from sodium carbonate. All other solvents and reagents were of reagent grade.

Synthesis:

The peptides were synthesized by the manual solid phase method as described [Folkers et al, 1984]. The peptides were cleaved from the resin with the concomitant removal of the protecting groups by treatment with doubly distilled HF at 0° C. for 1 h in the presence of about 10% p-cresol. The HF was then evaporated in vacuo. The residue was extracted 3 times with ether to remove non-peptidic material. The crude peptides were extracted with 20–50% aq. acetic acid and the extracts ere lyophilized.

Purification and Characterization:

Purification was achieved by gel filtration on Sephadex G-25 with 20% aqueous acetic acid as the eluent, followed by chromatography on Sephadex LH-20, 1–3 times with the solvent system, water: n-butanol: acetic acid: methanol 90:10:10:8. The purity was checked by TLC, amino acid analysis and HPLC. The peptides gave single spots on TLC in four different solvent systems (Table IV).

TABLE IV

DATA FOR LHRH ANTAGONISTS OF THE GENERAL SEQUENCE:
N—AC-( )¹, D-pClPhe², D-3-Pal³, Ser⁴, ( )⁵, ( )⁶, ( )⁷, ( )⁸, Pro⁹, D—Ala—NH₂¹⁰

| # | 1 | 5 | 6 | 7 | 8 | % AOA/µg dosage | | | TLC Data | | | |
|---|---|---|---|---|---|---|---|---|---|---|---|---|
| | | | | | | 0.125 | 0.25 | 0.5 | $Rf^1$ | $Rf^2$ | $Rf^3$ | $Rf^4$ |
| 1a | D-2-Nal | Tyr | D-NicLys | Leu | Arg | | | 60 | | | | |
| 2 | " | " | D-PicLys | " | " | | 0 | | 0.37 | 0.67 | 0.90 | 0.75 |
| 3 | " | PicLys | D-Tyr | " | " | | 0 | | 0.37 | 0.42 | 0.70 | 0.57 |
| 4 | " | Tyr | D-Trp | Val | " | | | 44 | 0.30 | 0.61 | 0.88 | 0.63 |
| 5 | " | c-PzACAla | " | Leu | " | | 17 | | 0.41 | 0.56 | 0.83 | 0.72 |
| 6 | " | " | D-Tyr | " | " | | | 50 | 0.37 | 0.58 | 0.83 | 0.73 |
| 7 | " | " | D-Qal | Val | " | | | 50 | 0.18 | 0.56 | 0.87 | 0.78 |
| 8 | " | PicLys | " | " | " | | | 25 | 0.43 | 0.54 | 0.96 | 0.56 |
| 9b | " | c-PzACAla | D-PicLys | Leu | ILys | 64 | 90 | | | | | |
| 10c | " | " | " | Val | " | | 12 | | | | | |
| 11 | " | " | " | Leu | Arg | | | 75 | 0.38 | 0.63 | 0.80 | 0.72 |
| 12 | " | " | " | Val | " | | 20 | 100 | 0.16 | 0.58 | 0.87 | 0.77 |
| 13 | " | PzaLys | " | " | " | | 0 | | 0.37 | 0.59 | 0.88 | 0.64 |
| 14de | D-3-Qal | c-PzACAla | " | Leu | ILys | 17 | 55 | 100 | | | | |
| 15f | " | " | " | " | Arg | 63 | 89 | | 0.31 | 0.63 | 0.70 | 0.58 |
| 16 | " | " | " | Val | " | 18 | | | 0.30 | 0.51 | 0.94 | 0.61 |
| 17 | " | PzcLys | " | " | " | | | 17 | 0.29 | 0.46 | 0.71 | 0.59 | aFrom Ljungqvist et al, 1987
bFrom Ljungqvist et al, 1990, 1988
cFrom Ljungqvist et al, 1990
dFrom Ljungqvist et al, 1991
e$ED_{50}$' 171 ± 17 µg/ml
f$ED_{50}$' 30.8 ± 0.59 µg/ml
Solvent Systems for TLC:
¹n-BuOH:HOAc:H₂O: 30:10:3:12
²n-BuOH:py:HOAc:H₂O: 5:5:1:3
³EtOAc:py:HOAc: 4:1:1:2
⁴n-BuOH:py:HOAc:H₂O: 4:1:1:2

Amino acid analyses were carried out on a Beckman 118CL Amino Acid Analyzer after hydrolysis in constant boiling HCl for 24 h using standard procedures [Folkers et al., 1984]. The unnatural amino acids were qualitatively determined with the exception of 3-Pal which was quantified. The results were in agreement with theory within the limites of experimental error. The purity was further checked by HPLC using a Waters Instrument with a 660 solvent programmer and a Vydac $C_{18}$ column. The flow rate was 1.5 ml/min and the absorbance was recorded at 210 nm. Different gradients of increasing concentration of acetonitrile in 0.01M $KH_2PO_4$, adjusted to pH 3 with $H_3PO_4$, were employed. All peptides were estimated to be 97–99% pure in this system.

Biological Assays:

The AOA was determined in rats as reported [Humphries et al.]. The in vitro histamine release test in rat mast cells was performed, as described [Hook et al., Karten et al., 1987], and the results are reported as $ED_{50}$ values which is the concentration in µg/ml that releases 50% of the total releasable histamine. The data from the determinations of AOA and $ED_{50}$ are in Table IV.

Based on the importance of the antagonist-receptor structural relationship, $Arg^8$ has been introduced in 13 new analogs towards achieving an increase in the AOA potency. Changes were made in positions 1, 5, 6 and 7 toward an increase in water solubility and a decrease in histamine release.

In position 1, D-3-Qal was used in three analogs. In position 5, c-PzACAla was used in 7 analogs. In position 6, D-PicLys, D-3-Qal, D-Trp, and D-Tyr were used as promising substituents. Leu in position 7 was frequently substituted by Val.

Based on analog 1 containing $Arg^8$ antagonists 2–8 were synthesized. Analog 2 contained D-PicLys instead of D-NicLys, and its AOA was 0%/0.25 µg. It was not tested at higher dose levels. In analog 3, amino acids in positions 5 and 6 were exchanged, but again, 0% AOA/0.25 µg was obtained. Analog 4 contained $D-Trp^6$, a substituent often used In this position in former years, but the activity of analog 5 was slightly lower than the AOA of the parent compound (peptide 1); 44% vs 60% at 0.5 µg.

Analogs 5 and 6 have large, rigid c-PzACAla in position 5. The activity of analog 5 with c-PzACAla⁵, $D-Trp^6$ was 17%/0.25 µg, while c-PzACAla⁵ in combination with $D-Tyr^6$ (analog 6) showed only 50% AOA/0.5 µg.

Analogs 7 and 8 have hydrophilic D-3-Qal in position 6, which is also weakly basic. Basic residues in position 6 were considered to increase potency. However, analogs 7 and 8 had only 50% and 25% activity at 0.5 µg, respectively.

The next analog chosen as a parent compound was peptide 9 [N-Ac-D-2-Nal¹, D-pClphe², D-3-Pal³, c-pzACAla⁵, D-PicLys⁶, ILys⁸, D-Ala¹⁰] LHRH with AOA of 90% at 0.5 µg and 64% at 0.25 µg. Its congener with $Val^7$ (peptide 10) was less potent and had 12% AOA at 0.25 µg.

Peptides 11 and 12 are analogs of peptides 9 and 10, respectively with Arg in position 8 instead of ILys, as the only difference. The activity of peptide 11 with $Leu^7$ decreased from 90 to 75% at 0.5 µg while the activity of peptide 12 with $Val^7$ increased from 12 to 20% at 0.25 µg. The same change in two different analogs might cause opposite changes in AOA.

Substitution of PzcLys⁵ instead of c-PzACAla⁵ was not successful in analog 13. These two amino acids contain the same pyrazine ring, but its distance from the s-carbon atom in c-PzACAla is longer by one more $CH_2$ group than for PzcLys, and also the substituent with the cyclohexyl nucleus is more rigid than the substituent with the straight chain, PzcLys. Analog 13 with PzcLys[5] showed 0% activity at 0.25 μg in comparison with 20% for its c-PzACAla[5] congener (peptide 12).

Peptide 14 [N-Ac-D-3-Qal[1], D-pClPhe[2], D-3-Pal[3], c-PzACAla[5], D-PicLys[6], ILys[8], D-Ala[10]] LHRH (21) is the best LHRH antagonist reported so far if considering both AOA and histamine release as well as water solubility. The Arg congener of this peptide (peptide 15) shows even higher AOA, 89% at 0.25 μg and 63% at 0.125 μg and maybe the most potent analog ever reported. This congener is named "Argtide". Substitution at Leu[7] by Val[7] decreased the activity sharply to 18% at 0.125 μg which is in contrast with peptides 11 and 12.

PzcLys in position 5 instead of c-PzACAla again resulted in the less active analog 17 with 17% AOA at 0.25 μg.

The histamine release was tested only for Argtide (peptide 15). The $ED_{50}$ value was 30.8±0.59 μg/ml, which seems quite promising, considering that both Arg and c-PzACAla are present in the sequence.

Both Antide and Argtide, described herein, have five D-amino acids. Argtide should have a long duration of action, comparable to that of Antide. Aubert et al. considered that the long-lasting effects of Antide are not due to an unusual receptor-affinity of Antide and that other effects need to be elucidated. Gordon et al. observed that low daily doses or slow-release implants of Antide may provide desirable therapy. Didolkar et al. observed that a sustained release formulation of Antide may provide the desirable physiological responses. Presumably, these observations are at least qualitatively applicable to Argtide.

EXAMPLE 3

DESIGN, SYNTHESIS AND BIOASSAYS OF ANALOGS OF ARGTIDE BY CRITERIA OF POTENCY AND SAFETY

The comparative data on six leading antagonists of investigators in the field are in Table V.

The natural amino acids were obtained from Advanced ChemTech, Louisville, Ky. Abu and Aze were purchased from Aldrich Chemical Co., Milwaukee, Wis., and were protected with the Boc-group by a standard method.

BOC-D-1-Nal, BOC-D-3-Qal, BOC-D-pClPhe, BOC-D-Pal and Boc-D-NicLys were all provided by Dr. Narasimba Rao of the Southwest Foundation for Biomedical Research, San Antonio, Tex. (under contract NO1-HD-1-3101 with NIH), and made available by the Contraceptive Development Branch, Center for Population Research, NICHD. BOC-Cis-L-aminocyclohexylalanine was also provided by Dr. Rao, and was converted to the corresponding BOC-Cis-L-PzACAla derivative by acylation with the p-nitrophenylester [Folkers et al., U.S. Pat. No. 4,935,491] of pyrazinecarboxylic acid in DMF. BOC-D- and L-PicLys, BOC-PzAPhe and BOC-D-PzcLys were similarly prepared from BOC-D- and L-Lys or BOC-APhe and picolinic- or pyrazine carboxylic acid p-nitrophenyl esters in DMF [Ljungqvist et al., 1988]. D-Cl₂Phe and D-pFPhe were prepared according to Rao et al.. The peptides ere synthesized as described [Ljungqvist et al., 1987].

The AOA was determined in rats, as reported (13). The in vitro histamine release test in rat mast cells was performed, as described [Hook et al.], and the results are reported as $ED_{50}$ values which is the concentration in μg/ml that released 50% of the total releasable histamine.

Thirteen analogs of Argtide, N-Ac-D-3-Qal,D-pClPhe, D-3-Pal, Ser,c-PzACAla, D-PicLys, Leu, Arg, Pro, D-AlaNH₂ [Janecka et al.] with single substitutions in position 2, 5, 6, 7 and 9 were synthesized and bioassayed toward more potent and safer antagonists (Table VI).

TABLE V

Comparison of Leading Antogonists.

| Name (Ref.) | Structure | 0.125 | 0.25 | 0.5 | 1.0 | 1.5 | $ED_{50}$ | Histamine release μg/ml |
|---|---|---|---|---|---|---|---|---|
| Nal-Arg (Rivier et al., 1984) | [N-Ac-D-2-Nal[1]; D-pFPhe[2], D-Trp[3], D-Arg[6]] LHRH | | | 50 | | | | 0.17 |
| Nal-Glu (Rivier et al., 1986) | [N-Ac-D-2-Nal[1], D-pClPhe[2], D-3-Pal[3], Arg[5], D-Glu(AA)[6], D-Ala[10]] LHRH | | | 50 | 100 | | | 1.6 |
| Antide (Ljungqvist et al., 1987) | [N-Ac-D-2-Nal[1], D-pClPhe[2], D-3-Pal[3], NicLys[5], D-NicLys[6], ILys[8], D-Ala[10]] LHRH | | | 36 | 100 | | >300 | |
| Argtide (Janecka et al.) | [N-Ac-D-3-Qal[1], D-pClPhe[2], D-3-Pal[3], c-PzACAla[5], D-PicLys[6], D-Ala[10]] LHRH | 63 | 89 47-41 | | | | 31 | |
| SB-75 (Bajusz et al.) | [N-Ac-D-2-Nal[1], D-pClPhe[2]D-3-Pal[3], D-Cit[6], D-Ala[10]] LHRH | | | | 75 | | | 1.5 |
| RS-26306 (Nestor et al.) | [N-Ac-D-2-Nal[1], D-pClPhe[2], D-3-Pal[3], D-hArg(Et₂)[6], hArg(Et)₂[8], D-Ala[10]] LHRH | | | 50 | | | 13 | |

This Example describes further designs toward safe and more potent LHRH antagonists.

TABLE VI

Data for Analogs of General Sequence:
N—Ac—D-3-Qal$^1$, ( )$^2$, D-3-Pal$^3$,
Ser$^4$, ( )$^5$, ( )$^6$, ( )$^7$, Arg$^8$, ( )$^9$, D—Ala$_{10}$—NH$_2$

| # | 2 | 5 | 6 | 7 | 9 | AOA %/μg 0.125 | ED$_{50}$ histamine release 0.25 μg/ml |
|---|---|---|---|---|---|---|---|
| 1$^a$ | D-pClPhe | c-PzACAla | D-Piclys | Leu | Pro | 63 | 89 30.8 ± 0.59 |
| 2 | D-Ptf | " | " | " | " | 20 | 100 22 ± 2.3 |
| 3 | D-Cl$_2$Phe | " | " | " | " | 0 | |
| 4 | D-pClPhe | PzAPhe | " | " | " | 33 | |
| 5 | " | PicLys | " | " | " | 0 | |
| 6 | " | Cit | " | " | " | 29 | 94 ± 12 |
| 7 | " | c-PzACAla | D-Pal | " | " | 0 | |
| 8 | " | " | D-Trp | " | " | 50 | |
| 9 | " | " | D-PzcLys | " | " | 50 | |
| 10 | " | " | D-Nal | " | " | 0 | |
| 11 | " | " | D-NicLys | " | " | 67 | |
| 12 | " | " | D-PicLys | Phe | " | 20 | |
| 13 | " | " | " | Abu | " | 29 | 40 ± 5.4 |
| 14 | " | " | " | Leu | Aze | 60 | 14 ± 1.8 |

$^a$From Janecka et al.

Bioassays.

The very large number of bioassays which are required for a very large number of samples necessitate a minimal number of animals for the initial bioassays. In these initial bioassays, relatively small differences in potencies, expressed as percent AOA, may be "semi-quantitative," but even such small initial differences may reveal valid trends of potency for structural interpretation and new designs.

Bioassays are repeated as many times as required for quantitative data. For example, three repeat bioassays on Argtide gave potencies of 47, 50, and 71% at 0.25 μg., and these tests were only at this dosage. The initial bioassay of Antide showing 63% at 0.125 μg and 89% at 0.25 μg was on the first sample of Argtide. The following three bioassays were on a resynthesized sample. However, both samples fulfilled all criteria for purity.

Position 2.

D-Ptf and D-Cl$_2$ were introduced. The best result was obtained for peptide 2 with D-Ptf (20% AOA/0.125 μg and 100% AOA/0.25 μg. The ED$_{50}$ was 22 μg/ml; the ED$_{50}$ of Argtide was 31 μg/ml.

Position 5.

c-PzACAla was replaced by PzAPhe, PicLys and Cit. Peptide 4 has PzAPhe$^5$ the aromatic congener of c-PzA-CAla, and the AOA was 33%/0.25 μg vs. 88% of Argtide. The rigid cyclohexylalanine in its cis-configuration has been much more effective in position 5 than the polar, aromatic PzAPhe. PicLys in this combination was inferior. Peptide 5 was inactive at 0.25 μg. Analog 6 with Cit showed one third of the potency of Argtide, but its ED$_{50}$ was 94 μg/ml, three times the value of Argtide.

Position 6.

D-PicLys was substituted by D-3Pal, D-Trp, D-PzcLys, D-2-Nal and D-NicLys. Peptides 7 and 10 with D-3-Pal and D-2-Nal, respectively, were inactive at 0.25 μg. D-Trp is neutral and D-PzcLys is less basic than D-PicLys. These amino acids might be a good choice for lowering histamine release. Analog 11 with D-NicLys showed 67% AOA/0.25 μg which confirms past results that picolinic acid is superior to nicotinic acid for acylation of lysine.

Position 7.

Phe and Abu were substituted for Leu. The hydrophilicity of Argtide was a reason for incorporating Phe in this position. The ideas was to balance the hydrophilicity with some strongly lipophilic amino acid. The AOA of peptide 12 with Phe$^7$ was 20%/0.25 μg. The aromaticity or steric nature of Phe might be responsible for the low potency. Abu in peptide 13 caused a decrease of AOA to 29% at 0.25 μg. The ED$_{50}$ was at 40 μg/ml.

Position 9.

Incorporation of Aze with the four-membered ring instead of Pro lowered the AOA of analog 14 from 89 to 60% at 0.25 μg. It may be that Pro$^9$ is not as necessary as is usually assumed. Aze might also be less susceptible to post-proline cleaving enzymes.

In Table VII, are data on the comparison of peptides with Arg$^8$ and ILys$^8$.

TABLE VII

Comparison of AOA and ED$_{50}$ Analogs with Arg$^8$ and ILys$^8$
N—Ac—D-3-Qal$^1$, ( )$^2$, D-3--Pal$^3$,
Ser$^4$, c-PzACAla$^5$, ( )$^6$, ( )$^7$, ( )$^8$, ( )$^9$, D—Ala$^{10}$NH$_2$

| # | 2 | 6 | 7 | 8 | 9 | AOA %/μg 0.125 | ED$_{50}$ histamine release 0.25 μg/ml |
|---|---|---|---|---|---|---|---|
| 1$^a$ | D-pClPhe | D-PicLys | Leu | Arg | Pro | 63 | 89 30.8 ± 0.59 |

TABLE VII-continued

Comparison of AOA and $ED_{50}$ Analogs with $Arg^8$ and $ILys^8$
N—Ac—D-3-Qal$^1$, ( )$^2$, D-3--Pal$^3$,
Ser$^4$, c-PzACAla$^5$, ( )$^6$, ( )$^7$, ( )$^8$, ( )$^9$, D—Ala$^{10}$NH$_2$

| # | 2 | 6 | 7 | 8 | 9 | AOA %/μg 0.125 | $ED_{50}$ histamine release 0.25 μg/ml |
|---|---|---|---|---|---|---|---|
| 1$^b$ | D-pClPhe | D-PicLys | " | ILys | " | 20 | 55 30.8 ± 0.59 |
| 2 | " | " | " | Arg | " |  | 100 171 ± 17 |
| 2$^1$ | D-Ptf | " | " | ILys | " |  | 20 22 ± 2.3 |
| 9 | " | D-PzcLys | " | Arg | " |  | 50 132 ± 18 |
| 9$^1$ | D-pClPhe | " | " | ILys | " |  | 17 |
| 13 | " | D-NicLys | " | Arg | " |  | 67 |
| 13$^1$ | D-pClPhe | " | " | ILys | " |  | 17 |
| 16 | " | D-PicLys | Abu | Arg | " |  | 29 |
| 16$^1$ | " | " | " | ILys | " |  | 11 |
| 17 | " | " | Leu | Arg | Aze |  | 60 14 ± 1.8 |
| 17$^1$ | " | " | " | ILys |  |  | 40 57 ± 6.1 |

$^a$From reference Janecka et al.
$^b$From reference Ljungqvist et al. 1991

For peptides 2, 9, 11, 13 and 14 i Table VI, their congeners with ILys$^8$ were synthesized and bioassayed. For each pair of antagonists, the AOA value was significantly higher for Arg$^8$ than for ILys$^8$, Histamine release was measured only for 3 pairs, and the $ED_{50}$ values were 4–6 times higher for the congeners with ILys$^8$ than with Arg$^8$.

TABLE VIII

Comparison of AOA of Analog with D-3-Qal$^1$ and p-2-Nal$^1$
N—Ac-( )$^1$, D-pClPhe$^2$, D-3-Pal$^3$,
Ber$^4$, ( )$^5$, ( )$^6$, ( )$^7$, Arg$^8$,
Pro$^9$, D—Ala$^{10}$—NH$_2$.

| # | 2 | 5 | 6 | 7 | AOA %/μg 0.125 | 0.25 | 0.5 |
|---|---|---|---|---|---|---|---|
| 1$^a$ | D-3-Qal | c-PzACala | D-PicLys | Leu | 63 | 89 |  |
| 1"$^a$ | D-2-Nal | " | " | " |  | 75 |  |
| 7 | D-3-Qal | " | D-3-Pal | " |  | 0 |  |
| 7" | D-2-Nal | " | " | " |  | 13 |  |
| 8 | D-3-Qal | " | D-Trp | " |  | 40 |  |
| 8"$^a$ | D-2-Nal | " | " | " |  | 17 |  |
| 15$^a$ | D-3-Qal | " | D-PicLys | Val | 18 |  |  |
| 15"$^a$ | D-2-Nal | " | " | " |  | 20 | 100 |
| 16$^a$ | D-3-Qal | PzcLys | " | " |  | 17 |  |
| 16"$^a$ | D-2-Nal | " | " | " |  | 0 |  |

$^a$from reference Janecka et al.

Data on AOA for analogs with D-2-Nal$^1$ and D-3-Qal$^1$ are in Table VIII. Of five pairs of these antagonists, four pairs with D-3-Qal were superior.

The following citations are incorporated in pertinent part by reference herein for the reasons cited in the above text.

References

Amoss et al., (1971) *Biochem. Biophys. Res. Commun.* 44: 205–210.
Aubert et al., (1991) Abs. 1688, 73, Am. Endocr. Soc. Meeting, June 19–22, Washington, D.C.
Bajusz et al., (1988) *Int. J. Peptide Protein Res.* 32: 425–435.
Bajusz et al., (1988) *Proc. Natl. Acad. Sci. USA* 85, 1637–1641.
Danforth et al., J. Clin. Endocrin. Metabl. 70, 554 (1990).
Didolkar et al., (1991) Abs. 1704, 73, Am. Endrocr. Soc. Meeting, June 19–22, Washington, D.C.
Dutta, Drugs of the Future 13, 761 (1988).
Edelstein et al., Contraception 42, 209 (1990).
Folkers et al., (Jun. 19, 1990) U.S. Pat. No. 4,935,491.
Folkers et al., Biochem. Biophys. Res. Commun. 123, 1221 (1984).
Folkers et al., (Jun. 19, 1990) U.S. Pat. No. 4,935,491.
Folkers et al., (1986) *Biochem. Biophys. Res. Comm.* 737, 709–715.
Freidinger et al., Science 210, 656 (1980).
Freidinger et al., J. Org. Chem. 47 104 (1982).
Gordon et al., (1991) Abs. 1212, 73, Am. Endocr. Soc. Meeting, June 19–22, Washington, D.C.
Hahn et al., (1985) *Life Sci.* 37, 505–509.
Hook et al., Fed. Proc. Am. Soc. Exptl. Biol. 44, 1323 (1985).
Hook et al., (1985) *Fed. Proc.* 44: 1323.
Horvath, et al., (1982) *Peptides* 3, 969–973.
Humphries et al., *Biochem. Biophys. Res. Comm.* (1976) 72, 939–944.
Humphries et al., (1987) *J. Med. Chem.* 21, 120–123.
Janecka et al., (1991) *Biochem. Biophys. Res. Comm.* 180:374
Joule et al., Heterocyclic Chemistry, p. 123, Van Nostrand Reinhold, Ondon (1972).
Karten et al. , (1986) *Endocr. Rev.* 7: 44–66.
Karten et al., in: LHRH and its Analogs: Contraceptive and Therapeutic Applications II, pp. 179–190, MTP Press LTD, Lancaster, England (1987).
Leal et al., J. Clin. Endocrin. Metab. 67, 1325 (1988).
Leal et al., Contraception 40 623, (1989).
Lee et al., Life Sci. 45 697 (1989).
Ljungqvist et al., (1988) Acta Chem. Scand. 842: 408–410.
Ljungqvist et al., (1987) Biochem. Biophys. Res. Comm. 148: 849–856.
Ljungqvist et al., Proc. Natl. Acad. Sci. USA 85, 8236 (1988).
Ljungqvist et al., (1990) Tetrahedron 46, 3297–3304.
Ljungqvist et al., (1991) Z. Naturforsch. 46b:1231.
Lunenfeld et al., Eds., *The Current Status of GnRH Analogues*, (1991) Parthenon Publishing Group, Park Ridge, N.J., p. 13–14.
Miller et al., J. Pharmaceut. Sci. 79 490 (1990).
Morgan, et al., (1986) *Into Arch. Allergy Appt. Immunol.*, 80, 70–74.

Moroder et al., Hoppe-Seyler's Z. Physiol. Chem. 357, 1651 (1976).
Nekola et (1984) *Clin. Res.* 32 865–869.
Nestor, Jr. et al., (1988) *Peptides:* 592–594.
Peterman et al., Helv. Chim. Acta 66, 1513 (1983).
Phillips et al., Life Sci. 43, 883 (1988).
Rao et al., (1987) *Int. J. Peptide Protein Res.* 29: 118–125.
Rivier et al., (1984) *LHRH Analogs as Antiovulatory Agents.* In: Vickery, B. H. and Nestor, Jr. J. J. Hofer, E. S. E., eds. LHRH and its Analogs MTP press, Lancaster, U.K. 11–22.
Rivier et al., (1986) *J. Med. Chem.* 29: 1846–1851.
Roeske et al., (1987) *LHRH and its Analogs*, Vickery, B. H. and Nestor, J. J., Jr., eds., MTP Press, Lancaster, U.K., pp. 17–24.
Schally et al., (1971) *Science* 173" 1036–1038.
Schmidt et al., (1984) *Contraception* 29: 283–289.
Sundaram et al., Agents and Actions 25, 307 (1988).

What is claimed is:

1. N-AcD-3-Qal$^1$,DpC1Phe$^2$, D-3-Pal$^3$, Ser$^4$,c-PzACAla$^5$, DPicLys$^6$, Leu$^7$, Arg$^8$, Pro$^9$DalaNH$_2$$^{10}$.

2. N-Ac-D-3-Qal$^1$, D-pClPhe$^2$, D-3-Pal$^3$, Ser$^4$, cPzACAla$^5$, D-PicLys$^6$, Leu$^7$, ILys$^8$, Pro$^9$, D-Ala$^{10}$-LHRH.

3. N-Ac-D-2-Nal$^1$, D-pClPhe$^2$, D-3-Pal$^3$, Ser$^4$, PicLys$^5$, D-(DSer)Lys$^6$, Leu$^7$, ILys$^8$, Pro$^9$, D-Ala$^{10}$-LHRH.

4. N-Ac-D-2-Nal$^1$, D-pClPhe$^2$, D-3-Pal$^3$, Ser$^4$, c-PzACAla$^5$, D-PzAla$^6$, Leu$^7$, ILys$^8$, Pro$^9$, D-Ala$^{10}$-LHRH.

* * * * *

UNITED STATES PATENT AND TRADEMARK OFFICE
CERTIFICATE OF CORRECTION

PATENT NO.    :   5,480,969
DATED         :   January 2, 1996
INVENTOR(S)   :   Cyril Y. Bowers, Karl A. Folkers, Anders Ljungqvist, Dong-Mei Feng, and Anna Janecka It is certified that error appears in the above-identified patent and that said Letters Patent is hereby corrected as shown below:

On the title page of the patent, item [75] Inventors: delete the name "Janceka" and insert the name --Janecka-- therefor.

In claim 1, Column 20, lines 5-6, delete the term "PzACAla$_5$" and insert the term --PzACAla$^5$-- therefor.

Signed and Sealed this

Nineteenth Day of March, 1996

Attest:

BRUCE LEHMAN

*Attesting Officer*    *Commissioner of Patents and Trademarks*